(12) United States Patent
Stockel et al.

(10) Patent No.: US 8,193,244 B1
(45) Date of Patent: Jun. 5, 2012

(54) ANTIMICROBIAL AGENTS

(75) Inventors: Richard F. Stockel, Bridgewater, NJ (US); Anthony Joseph Sawyer, Oakton, VA (US)

(73) Assignee: Nevada Naturals, Inc., Albuquerque, NM (US)

( * ) Notice: Subject to any disclaimer, the term of this patent is extended or adjusted under 35 U.S.C. 154(b) by 244 days.

(21) Appl. No.: 12/455,197

(22) Filed: May 28, 2009

Related U.S. Application Data

(60) Provisional application No. 61/130,225, filed on May 29, 2008.

(51) Int. Cl.
*A61K 31/215* (2006.01)
*A61K 31/24* (2006.01)
*A61K 8/02* (2006.01)
*A01N 25/00* (2006.01)

(52) U.S. Cl. ......... 514/529; 514/534; 424/401; 424/405

(58) Field of Classification Search .................. 514/529, 514/534; 424/401, 450, 405
See application file for complete search history.

(56) References Cited

U.S. PATENT DOCUMENTS

| | | | |
|---|---|---|---|
| 3,825,560 A | 7/1974 | Saito et al. | |
| 4,997,851 A | 3/1991 | Isaacs et al. | |
| 5,434,182 A | 7/1995 | Isaacs et al. | |
| 5,780,658 A | 7/1998 | Martinez-Pardo et al. | |
| 6,414,023 B1 | 7/2002 | Brandsborg et al. | |
| 6,475,537 B1 * | 11/2002 | King et al. | 424/778 |
| 6,638,978 B1 | 10/2003 | Kabara | |
| 7,074,447 B2 | 7/2006 | Bonaventura et al. | |
| 7,087,769 B1 | 8/2006 | Contijoch Manent et al. | |
| 2004/0122095 A1 | 6/2004 | Seguer Bonaventura et al. | |
| 2004/0166082 A1 | 8/2004 | Urgell-Beltran et al. | |
| 2004/0175350 A1 | 9/2004 | Urgell Beltran et al. | |
| 2004/0254232 A1 | 12/2004 | Urgell Beltran et al. | |
| 2004/0265443 A1 | 12/2004 | Urgell Beltran et al. | |
| 2005/0084471 A1 | 4/2005 | Andrews | |
| 2005/0175747 A1 | 8/2005 | Seguer Bonaventura et al. | |
| 2006/0030512 A1 | 2/2006 | Hart | |

FOREIGN PATENT DOCUMENTS

WO  WO/2008/014824  2/2008

* cited by examiner

*Primary Examiner* — Shengjun Wang
(74) *Attorney, Agent, or Firm* — Frenkel & Associates, PC

(57) ABSTRACT

The combination of $N^\alpha$-long chain alkanoyl di basic amino acid alkyl ester salts with glycerol monofatty acid esters results in biocidal synergy and the extension of cidal activity of the di basic amino acid derivative for a variety of antimicrobial applications like oral care, wound care, dermatological care, animal care, and cosmetic applications.

$N^\alpha$-C8-C14-long chain alkanoyl-L-arginine alkyl (C1-C4 short chain) ester salts with glycerol monofatty acid esters (C8-C14) are very effective as antimicrobial agents for hospital use particularly as a coating for surgical drapes, covers, walls, trays, table tops, gurneys, or the like. Other uses include the treatment of HSV-1 (fever sore) and as a microbicide when using the combination of the di basic amino acid ester derivative with glycerol monofatty acid esters for preventing HIV and STD's.

9 Claims, No Drawings

ANTIMICROBIAL AGENTS

REFERENCE TO RELATED APPLICATIONS

This application claims the benefit of provisional application Ser. No. 61/130,225 filed May 29, 2008.

INTRODUCTION—BACKGROUND

This invention discloses the use of certain $N^\alpha$-long chain (C8 to C16) alkanoyl di basic amino acid alkyl (C1 to C4) ester salts with fatty acid ($C_8$-$C_{14}$) glycerol esters. Specifically the $N^\alpha$-long chain alkanoyl di basic amino acid alkyl ester salts of interest are the $N^\alpha$-long chain alkanoyl dibasic amino acid alkyl ester of L-arginine, L-histidine, L-tryptophan and L-lysine. The corresponding anion can be any anions that do not cause significant water insolubility and thereby prevent its effectiveness as an antimicrobial agent in aqueous or alcoholic solvents. Suitable anions include but are not limited to halides, sulfate, acetate, glycerophosphate, gluconate, mono- di- or tri-carboxylic acid, hydroxy carboxylic acid or mono and dihydrogen phosphates, phosphonates, phosphinates, and phenolates.

Although $N^\alpha$-long chain alkanoyl di basic amino acid alkyl ester salts have been known since the 1960's, one of the first patents to recommend these amino acids, specifically for food applications was U.S. Pat. No. 3,825,560 (issued Jul. 23, 1979). A number of derivatives are disclosed including $N^\alpha$-cocoyl-L-arginine ethyl ester pyrrolidone carboxylate and $N^\alpha$-lauroyl-L-arginine methyl ester hydrochloride. Since this publication there has been several more patents issued or published disclosing specifically $N^\alpha$-lauroyl-L-arginine ethyl ester hydrochloride salt (LAE). These include U.S. Pat. No. 5,780,658 that discloses a process to prepare LAE, as well as disclosing its use for food applications. U.S. Pat. No. 7,074,447 B2 discloses an antimicrobial composition comprising LAE with potassium sorbate. U.S. Pat. No. 7,087,769 is another process patent suggesting its use for food. Two patent publications, U.S. 2004/0166082 and U.S. 2004/0175350, disclosure di basic amino acid alkyl ester salts useful for cosmetic applications. U.S. 2004/0254232 covers oral care while U.S. 2004/0265443 covers food. U.S. 2005/0175747 discloses complexes formed between LAE and various anionic hydrocolloids. All of the above references are incorporated into the body of our present invention.

One of the purposes of this invention is to formulate a synergistic $N^\alpha$-long chain alkanoyl di basic amino acid alkyl ester salt type biocide mixture that will overcome a significant shortcoming found in the sole use of $N^\alpha$-long chain alkanoyl di basic amino acid alkyl ester salts. By combining glycerol esters of fatty acids, with chain lengths of from $C_6$ to $C_{14}$, significant broadening of cidal activity is found for the $N^\alpha$-long chain alkanoyl di basic amino acid alkyl ester salts. Furthermore, this synergistic composition allows the use of much lower levels of either biocide while maintaining biocidal efficacy and thereby reducing cost.

A shortcoming of $N^\alpha$-long chain alkanoyl di basic amino acid alkyl ester salts are their loss of anti-microbial activity and water solubility due to chemical/enzymatic hydrolysis of the ester functionality. This loss is dependent on a number of variables e.g., presence of lipases and/or esterases, and pH. It has been found that the chemical hydrolysis is particularly rapid at about pH4.0 or below or at about pH8.0 or above. Because in many applications the pH is in these critical ranges, $N^\alpha$-long chain alkanoyl di basic amino acid alkyl ester salts need to have present other bioactive substances to maintain activity after the $N^\alpha$-long chain alkanoyl di basic amino acid alkyl ester salts have hydrolyzed.

Also, $N^\alpha$-long chain alkanoyl di basic amino acid alkyl ester salts have a strong tendency to form complexes, since they have a guanidine chelating ligand. Both entropy and enthalpy thermodynamic properties are favored with $N^\alpha$-long chain alkanoyl di basic amino acid alkyl ester salts due to their potential formation of 5 and 6 membered rings with heavy metal ions. Furthermore, $N^\alpha$-long chain alkanoyl di basic amino acid alkyl ester salts readily react with anionic species e.g., carboxylates, acidic amino acids, proteins having a residual negative charge, phosphato groups on nucleotides of DNA, anionic phospholipids, hydroxycarboxylates, phenolates, phosphonates, and phosphinates to give salts of low water solubility.

The second component of the synergistic system of this invention is a glyceryl monoalkanoate ester (acyl monoglyceride) having from 6 to 14 carbon atoms. Glyceryl monoalkanoates have a long history of safety and a low toxicity profile.

The literature is replete with numerous references concerning glycerol monofatty acid esters having antiviral and antibacterial activity. The most active monoglycerides consist of those esters formed from saturated fatty acids having from 6 to 14 carbon atoms. U.S. Pat. No. 4,997,851 teaches the use of saturated fatty acids and glycerol monofatty acid esters as effective antiviral agents against the HIV and HSV-1 viruses. They were also active against a variety of gram positive and gram-negative bacteria. U.S. Pat. No. 5,434,182 discloses the spermicidal, antimicrobial and cytocidal activity of glycerol monofatty acid esters.

It discloses the combination of fatty acyl glycerides, a chelating acid, and a surfactant which confer excellent antimicrobial activity for preserving processed meats and for disinfecting poultry carcasses. When only one of these three agents was used, the anti-microbial performance was considerably reduced. U.S. Pat. No. 6,414,023 B1 discloses the use of fatty acid monoglycerides in conjunction with 2,4-dichlorobenzyl alcohol.

John J. Kabara in U.S. Pat. No. 6,638,978 B1 lists a preservative formulation for food and cosmetics consisting of monolaurin (ML), caprylic and capric acid mixture, and propylene glycol in an aqueous base. U.S. 2005/0084471 A1 teaches the preparation of a preservative for meat, fruits, and vegetables and for the disinfection of inanimate surfaces. The actives include a propylene glycol C7-C14 fatty acid ester as the major component, a surfactant, and an enhancer. Enhancers include phenolic antioxidants and/or a paraben ester. Lastly, U.S. Patent 2006/0030512 A1 describes a long lasting anti-microbial film comprising a glycerol monoester, an amphoteric surfactant, a chelating agent and a solvent like propyl alcohol plus other incipients. All of the above references are incorporated into the body of our present invention.

PURPOSE OF THE INVENTION

In addition to the outstanding antimicrobial properties of $N^\alpha$-long alkanoyl di basic amino acid alkyl ester salts, these salts are especially safe for humans and the environment. They completely biodegrade into endogenous natural products resulting in very low overall toxicity for both humans and the environment.

One drawback of $N^\alpha$-long chain alkanoyl di basic amino acid alkyl ester salts are that they are strongly positively charged, due to the guanidine group. This group retains its charge even in alkaline aqueous solutions. The isoelectric point of the guanidine group in L-arginine is about pH 10-11.

This causes $N^\alpha$-long chain alkanoyl di basic amino acid alkyl ester salts to react with many negatively charged molecules found in various foods like basic amino acids, negatively charged nucleotides, polysaccharides, enzymes, etc.

The interaction of oppositely charged species is both kinetically and thermodynamically dependent. Thus the loss of $N^\alpha$-long chain alkanoyl di basic amino acid alkyl ester salts by this mechanism will occur at various rates depending on the micro-environment.

This invention teaches the use of glycerol monofatty acid esters (acyl monoglycerides) as co-biocides with $N^\alpha$-long chain alkanoyl di basic amino acid alkyl ester salts to provide several advantages not observed by using $N^\alpha$-long chain alkanoyl di basic amino acid alkyl ester salts alone.

The use of combinations of $N^\alpha$-long chain alkanoyl di basic amino acid alkyl ester salts with glycerol monofatty acid esters have several advantages over other antimicrobials such as:

Their high cost effectiveness
Their lack of toxicity
Their broad spectrum of activity, which is further extended with glycerol monofatty acid esters to include HIV, HSV-1, and other viruses and fungi.
Their easy application from solution in water, water/lower alcohol, or lower alcohol by dipping, spraying or other techniques.

By microbial and organoleptic testing it has been found that the synergistic combination of $N^\alpha$-long chain alkanoyl di basic amino acid alkyl ester salts with glycerol monofatty acid esters has resulted in several improvements as listed below:

Broadening of antimicrobial activity
Lengthening of time that the solutions retain antimicrobial activity
Improved cost-effectiveness
The production of organolepticly satisfying products Experimentally, it has been found that the level of $N^\alpha$-long chain alkanoyl di basic amino acid alkyl ester salts can be from about 10 to about 500 ppm, preferably from about 75 to about 300 ppm, and most preferably from about 100 ppm to about 250 ppm. By practicing this invention the $N^\alpha$-long chain alkanoyl di basic amino acid alkyl ester salts level can be reduced from about 50 to about 150 ppm rather than the normally much higher levels. Some organisms such as viruses, e.g. SARS, H1N1, etc., yeast, fungi, or mold might require the use of higher levels, possibly up to 1.0 wt %. However to function as a preservative the usage level may have to be as high as 5000 ppm depending on what other ingredients are present in a particular formulation.

It has also been found that the level of glycerol monofatty acid esters, having a carbon chain length of $C_8$ to $C_{14}$, as the co-biocide is most effective with from about 25 to about 75 ppm or higher in the case of preservation of cosmetics and up to 500 ppm depending on what other ingredients are present in the particular cosmetic formulation. Some organisms such as viruses, e.g. SARS, H1N1, etc., yeast, fungi, or mold might require higher use levels, possibly up to 2.0 wt. %. Compositions of this invention can be effective in the pH range between about 2 and 10.0. However, at pHs of about 4.0 and lower and at 9.0 and higher the $N^\alpha$-long chain (C8 to C16) alkanoyl di basic amino acid alkyl (C1 to C4) ester salts tend to hydrolyze. Therefore a more ideal pH range for their use is between 4.0 and 9.0.

Surfactants

Certain applications for $N^\alpha$-long chain alkanoyl di basic amino acid alkyl ester salts with glycerol monofatty acid esters will require a surfactant to solubilize all of the ingredients in a particular formulation.

Experimentally, it has been determined that the preferred surfactants, which form micelles, microemulsions, nanoemulsions, or emulsions with the compositions of this invention, are by and large, either of the amphoteric and non-ionic type, or combinations thereof. Highly charged anionic surfactants have the potential to reduce the overall bioactivity of these complexes by causing some degree of precipitation of the cationic $N^\alpha$-long chain alkanoyl di basic amino acid alkyl ester salts, thereby lessening its effective.

It was also found that certain cationic surfactants, sometimes in combination with non-ionic and/or amphoteric surfactants are effective in forming stable emulsions and/or microemulsions.

Surfactants that carry a positive charge in strongly acidic media, carry a negative charge in strongly basic media, and form zwitterionic species at intermediate pH's are amphoteric. The preferred pH range for compatibility with compositions of this invention is in the acidic or neutral ph range of from about 2.0 to about 9.0. Under this pH range the amphoteric surfactant is mostly cationic or zwitterionic (overall neutral charge) form. In the more alkaline range where it is anionic it may dilute the bioactivity of the compositions of this invention.

There are several classes of amphoteric surfactants useful for preparing microemulsions or emulsions for the complexes of this invention. These include but are not limited to:

N-alkylamino acids
alkyldimethyl betaines
alkylamino betaines
alkyl amphoacetates
alkyl amphopropionates
sulfobetaines
imidazolines
amino or imino propionates Some of the above amphoteric surfactants have moderate to good antimicrobial activity against certain microorganism especially in acidic media, and hence can be synergistic with systems of this invention.

Nonionic surfactants have also been found to be useful to form small particle micelles for these complexes. The advantage of small micelles is the ability to use lower concentrations while maintaining efficacy. Nonionic surfactants include but are not limited to the following:

alcohols
alkanolamides
Amine oxides
Esters
ethoxylated(propoxylated)carboxylic acids
ethoxylated(propoxylated)glycerides
glycol esters (and derivatives)
mono(di)glycerides
polyglycerol esters
polyhydric alcohol esters and ethers
sorbitan/sorbital esters
di(tri)esters of phosphoric acid
Esters
ethoxylated(propoxylated)alcohols
ethoxylated(propoxylated)lanolin
ethoxylated(propoxylated)polysiloxanes
ethoxylated-propoxylated block copolymers Two suitable cationic surfactants include D,L-2-pyrrolidone-5-carboxylic acid salt of ethyl-N-cocoyl-L-arginate (CAE), marketed by Ajinomto and cocamidopropyl, cocamidopropyl PG dimonium chloride phosphate (PTC), marketed by Uniqema, and the like.

It has been found experimentally that using combinations or singular surfactants, an effective range can consist of 0.01 to 10 wt %, preferably 0.1 to about 5 wt. %, based on the particular bioactives in the formulation.

Solvents

Solvents that are useful for this invention should preferably be non-toxic and classified as GRAS acceptable. They should also be non-irritating and have excellent solubility properties for all of the ingredients found in the formulations used in this invention. Some non-exclusive examples include ethanol, glycerin, sorbitol, polyethylene glycols, propylene glycol, glycerol monoesters ($C_1$-$C_{10}$), triacetin, polysorbate and the like. Combination of these solvents can also be used.

EX. 1

The following demonstrates the synergistic preservative action of Nα-lauroyl arginine ethyl ester salt (LAE) with glycerol monolaurate (monolaurin)

EXPERIMENTAL RESULTS

| Monolaurin ppm | LAE ppm 120 | 100 | 80 | 60 | 40 | 30 | 20 | 15 | 10 | 7.5 |
|---|---|---|---|---|---|---|---|---|---|---|
| 0   | 0 | 0 | 0 | 0 | 0  | 0  | G  | G | G | G |
| 10  | 0 | 0 | 0 | 0 | 0  | 0  | 0  | G | G | G |
| 20  | 0 | 0 | 0 | 0 | 0  | 0  | 0  | 0 | G | G |
| 30  | 0 | 0 | 0 | 0 | 0  | 0  | 0  | 0 | G | G |
| 40  | 0 | 0 | 0 | 0 | 0  | 0  | 0  | 0 | 0 | G |
| 50  | 0 | 0 | 0 | 0 | 0  | 0  | 0  | 0 | G | G |
| 60  | 0 | 0 | 0 | 0 | 0  | 0  | 0  | 0 | G | G |
| 70  | 0 | 0 | 0 | 0 | 0  | 0  | 0  | 0 | G | G |
| 80  | 0 | 0 | 0 | 0 | 0  | PT | PT | G | G | G |
| 90  | 0 | 0 | 0 | 0 | PT | PT | PT | G | G | G |
| 100 | 0 | 0 | 0 | 0 | PT | PT | PT | G | G | G |

0 = no growth
G = growth
PT = partial turbidity
organism is *Candida Albicans*

The results clearly indicate synergy between LAE and monolaurin as a combination preservative. Thus used in the amounts of 10 ppm LAE with 40 ppm Monolaurin, complete growth inhibition of candida albicans is obtained whereas when used alone, 30 ppm of LAE or much more than 100 ppm monolaurin would be required to achieve growth inhibition.

EX. 2

Time Kill Test at 90 seconds with a LAE concentration at 500 ppm and ML concentration at 45 ppm.

| Organism | Log Reduction |
|---|---|
| *Klebsiella pneumoniae* | >2.0 |
| *Pseudomonas aeruginosa* | >2.0 |

Equipment for handling blood products such as blood sera can be treated with effective amounts of antiviral or antibacterial active ingredients, for example, coated test tubes, vacutainer tubes, and other blood handling items. Other potential applications for the spermicidal, antimicrobial, cytocidal, and antibacterial properties of $N^\alpha$-long chain di-basic amino acid ester salts with a synergistic amount of a glycerol monofatty acid ester include: facial cream (as an acne treatment), bactericidal, fungicidal, virucidal; mold and mildewcide; shampoo, hand lotion; athlete's foot medication (ointment, powder, soap); candies and chewing gum (for sore throat, bad breath, recurrent herpes); ointment or foam spray (for genital herpes legion treatment); shaving cream; lip balm; mouth wash; after shave lotions; tooth paste; diaper rash preventer; plasma bag treatment; disposable glove treatment; additive to pasteurized cow milk; additive to blood sample tubes to inactivate HIV, HCMV, and other viruses (safety measure for lab technicians and healthcare providers); additives for condoms, band-aids, or bandages; feminine hygiene; additive for paint; or animal or plant treatment for microbial infections.

Where certain spermicidal, antimicrobial, cytocidal, or antibacterial usage is intended, a spermicidal, antimicrobial, cytocidal, or antibacterial effective amount of a $N^\alpha$-long chain alkanoyl di-basic amino acid alkyl ester salts with a synergistic amount of a glycerol monofatty acid ester is applied with a carrier to the outer or inner surface or surfaces of an appropriate vehicle. For example, a condom or diaphragm could be coated wholly or partially with dry or liquid, preferably, viscous, coating material containing a spermicidally effective amount of an $N^\alpha$-long chain alkanoyl di-basic amino acid alkyl ester salt with a synergistic amount of a glycerol monofatty acid ester according to the invention. In addition, an effective amount of the $N^\alpha$-long chain alkanoyl di-basic amino acid alkyl ester salts with a synergistic amount of a glycerol monofatty acid ester of the invention can be applied in admixture with other antimicrobially, cytocidally, antibacterially, and/or spermicidally active ingredients. For example, in a preferred embodiment the spermicide Nonoxynol-9 could be admixed with an effective amount of an $N^\alpha$-long chain alkanoyl di-basic amino acid alkyl ester salt with a synergistic amount of a glycerol monofatty acid ester of the invention either prior to or during application to a condom or diaphragm. Further, in some instances the compounds of the invention could be applied, alone or in admixture with another spermicide, topically or vaginally.

The purpose of admixing the components of the invention with a spermicide such as Nonoxynol-9 is to minimize the adverse effects, such as irritation, that have been associated with usage of such materials. Admixing Nonoxynol-9 with an effective portion of an $N^\alpha$-long chain alkanoyl di-basic amino acid alkyl ester salt with a synergistic amount of a glycerol monofatty acid ester according to the invention would permit use of reduced concentrations of Nonoxynol-9 and thus reduce or eliminate irritation.

Also, while reference is made to spermicidal, antimicrobial, cytocidal, or antibacterial activity, it should be noted that activity against sexually transmitted diseases (STD's) is intended. Such sexually transmitted diseases include, but are not limited to, herpes, chlamydia, syphilis, gonorrhea, HIV, and other retroviruses, such as HTLV-I and HTLV-II. Treatment or prevention could consist of topical or vaginal application of an effective amount of $N^\alpha$-long chain alkanoyl di basic amino acid alkyl ester salts with a synergistic amount of a glycerol monofatty acid ester according to the invention, in or on a suitable carrier. For example, a diaphragm, sponge, IUD, or other suitable device or substrate containing or having thereon an effective amount of active ingredient, may be positioned intravaginally. In some instances there may be topical application of an effective amount of active ingredient, for example, in the treatment of herpes sores. Such treatment or prevention could be carried out in combination with other active ingredients.

The literature is replete with a variety of antimicrobial agents useful to prevent infection in hospital settings. Another application for this invention would be for hand washing. The purpose of hand washing in the health care setting is to remove or destroy (disinfect) pathogenic microorganisms to avoid transmitting them to a patient. The application of water alone is ineffective for cleaning skin because water is unable to remove fats, oils, and proteins, which are components of organic soil. Therefore, removal of microorganisms from skin requires the addition of soaps or detergents to water. Plain soap does not kill pathogens. However, the addition of antiseptic chemicals to soap ("medicated" or "antimicrobial" soaps) does confer killing action to a hand washing agent. Such killing action may be desired prior to performing surgery or in settings in which antibiotic-resistant organisms are highly prevalent (WHO guidelines on Hand Washing in Health Care).

The proper washing of hands in a medical setting generally consists of the use of generous amounts of soap and water to lather and rub each part of ones hands systematically for 15 to 20 seconds. Hands should be rubbed together with digits interlocking. If there is debris under fingernails, a bristle brush is often used to remove it. Finally, it is necessary to rinse well and wipe dry with a paper towel. After drying, a dry paper towel should be used to turn off the water (and open any exit door if necessary).

To 'scrub' one's hands for a surgical operation, a tap that can be turned on and off without touching with the hands, some chlorhexidine or iodine wash as has been used, sterile towels for drying the hands after washing, and a sterile brush for scrubbing and another sterile instrument for cleaning under the fingernails are required. All jewellery should be removed. This procedure requires washing the hands and forearms up to the elbows, and one must in this situation ensure that all parts of the hands and forearms are well scrubbed several times. When rinsing, it is ensured at all times that one does not allow water to drip back from the elbow to your hands. When done hands are dried with a sterile cloth and a surgical gown is donned. Our invention would replace chlorhexidine and iodine with a mixture of an $N^\alpha$-long chain alkanoyl di basic amino acid alkyl ester salt such as LAE with a glycerol monofatty acid ester like monolaurin for either cleaning hands and forearms or pre-operative preparation of patients' skin. As a cation, LAE adheres to negatively charged skin better than a non-charged entity. $N^\alpha$-long chain alkanoyl di basic amino acid alkyl ester salt such as LAE with a glycerol monofatty acid ester such as monolaurin also do not have the known adverse toxicological effects of iodine-like compounds, e.g. Povidone iodine.

Useful medical applications of this invention include the treatment of HSV-1 (fever sore) and as a preventative barrier against bacteria when applied to surgical drapes. The latter include applications as interventional radiology and cardiology, urology, obstetrics and gynecology, orthopedics, neurosurgery, ophthalmic, ENT, CVOR, and general-purpose surgery.

Still another use would be as an effective microbicide against the spread of HIV or STD's used on a condom, anally, or vaginally. Significant protection would be found. It has been found experimentally that the LAE usage is generally in the range of 2.5 to 1000 ppm depending on the specific application. For treatment of a fever sore the range is from about 500 to about 1000 ppm, which for the drape application is from 25 to about 500 ppm. This would be significantly reduced in the presence of a glycerol monofatty acid ester with chain length of C8-C14. When virucidal activity needs to be enhanced, certain glycerol monofatty acid esters are added. These which have a carbon chain length of C8-C14 are preferred, and C12 (lauryl) is most preferred. The latter is known as monolaurin. The usage of monolaurin synergistically was found to be from about 1 to about 10 wt. percent, based on the di basic amino acid ester salt derivative. More preferably a range of about 1.5 to about 5.0 wt. % monolaurin is very effective.

Since monolaurin is not very water soluble, a surfactant is required to form a stable emulsion, nanoemulsion, or microemulsion. In general non-ionic, amphoteric, and cationic surfactants with an HLB between 8-20 have been found to be useful. When making a microemulsion a cosolvent is required. Some useful cosolvents are ethanol, methanol, isopropanol, propylene glycol, and other hydroxylic solvents. The surfactant is useful in the range of 1 to 10 wt. percent based on the antimicrobial agents. The various substrates in which the compositions of this invention can be applied are:

Paper
Woven fabric
Non-woven fabric
Knitted fabric
Polyolefins
Polyesters
Polyvinyl alcohol and copolymers thereof.

The preceding specific embodiments are illustrative of the practice of the invention. It is to be understood, however, that other expedients known to those skilled in the art or disclosed herein may be employed without departing from the spirit of the invention or the scope of the appended claims.

The invention claimed is:

1. A composition comprising $N^\alpha$-lauroyl-L-arginine ethyl ester hydrochloride salt and glycerol monolaurate at a synergistically effective antimicrobial ratio in an aqueous or non-aqueous solution.

2. The composition of claim 1 wherein the $N^\alpha$-lauroyl-L-arginine ethyl ester hydrochloride salt and glycerol monolaurate are present in the composition in a ratio of between about 9:1 to about 1:1 respectively, within which ratios the said combination of $N^\alpha$-lauroyl-L-arginine ethyl ester hydrochloride salt and glycerol monolaurate provide synergistic antimicrobial activity.

3. The composition of claim 1, wherein the $N^\alpha$-lauroyl-L-arginine ethyl ester hydrochloride salt and glycerol monolaurate are each present in an effective antimicrobial concentration between about 0.001 wt % and 2% wt %.

4. The composition of claim 1 which also optionally contains one or more non-ionic, cationic, or amphoteric surfactants in the range of about 0.1 to 5 wt. % based on the weight of the composition.

5. The composition of claim 1 which also contains a solvent comprising ethanol, propylene glycol, sorbitol, or polysorbate which is added to the final usage formulation in addition of any water present.

6. An antimicrobial composition as described in claim 1 whereby the final formulation has a pH of about 2.5 to about 6.0.

7. A method of inhibiting bacterial, fungi, mold, yeast, and virus growth by the application of a composition comprising $N^\alpha$-lauroyl-L-arginine ethyl ester hydrochloride salt and glycerol monolaurate to a surface or a solution, said composition showing synergistic activity of $N^\alpha$-lauroyl-L-arginine ethyl ester hydrochloride salt with glycerol monolaurate.

8. A method as described in claim 7, wherein the $N^\alpha$-lauroyl-L-arginine ethyl ester hydrochloride salt and glycerol monolaurate are present in the composition in a ratio of between about 9:1 to about 1:1 by wt. respectively, within which ratios the said combination of $N^\alpha$-lauroyl-L-arginine ethyl ester hydrochloride salt and glycerol monolaurate provide synergistic anti-microbial activity.

9. A method as described in claim 7, wherein the $N^\alpha$-lauroyl-L-arginine ethyl ester hydrochloride salt and glycerol monolaurate are each present in an effective antimicrobial concentration between about 0.001 wt % and 2% wt %.

* * * * *